(12) United States Patent
Bhat et al.

(10) Patent No.: US 10,040,775 B2
(45) Date of Patent: Aug. 7, 2018

(54) SYNTHESIS OF CHIRALLY ENRICHED 2,4-DISUBSTITUTED TETRAHYDROPYRAN-4-OL AND ITS DERIVATIVES

(71) Applicant: S.H. KELKAR AND COMPANY LTD., Mumbai, Maharashtra (IN)

(72) Inventors: Sujata V. Bhat, Mumbai (IN); Ravindra D. Gaikwad, Mumbai (IN); Kedar R. Vaze, Maharashtra (IN)

(73) Assignee: S.H. KELKAR AND COMPANY LTD., Mumbai, Maharashtra (IN)

( * ) Notice: Subject to any disclaimer, the term of this patent is extended or adjusted under 35 U.S.C. 154(b) by 0 days.

(21) Appl. No.: 15/519,855

(22) PCT Filed: Oct. 16, 2015

(86) PCT No.: PCT/IN2015/000390
§ 371 (c)(1),
(2) Date: Apr. 18, 2017

(87) PCT Pub. No.: WO2016/059648
PCT Pub. Date: Apr. 21, 2016

(65) Prior Publication Data
US 2017/0247349 A1    Aug. 31, 2017

(30) Foreign Application Priority Data
Oct. 18, 2014    (IN) .......................... 3333/MUM/2014

(51) Int. Cl.
| | | |
|---|---|---|
| *C07D 309/10* | (2006.01) | |
| *C11D 7/26* | (2006.01) | |
| *A61Q 15/00* | (2006.01) | |
| *C11B 9/00* | (2006.01) | |
| *A61K 8/49* | (2006.01) | |

(52) U.S. Cl.
CPC ............ *C07D 309/10* (2013.01); *A61K 8/498* (2013.01); *A61Q 15/00* (2013.01); *C11B 9/008* (2013.01); *C11D 7/267* (2013.01)

(58) Field of Classification Search
CPC ...... C07D 309/10; C11D 7/267; A61K 8/498; C11B 9/008; A61Q 15/00
See application file for complete search history.

(56) References Cited

U.S. PATENT DOCUMENTS

| | | | |
|---|---|---|---|
| 2011/0306779 A1 | 12/2011 | Gralla et al. | |
| 2014/0107352 A1 | 4/2014 | Stork et al. | |

FOREIGN PATENT DOCUMENTS

| | | | | |
|---|---|---|---|---|
| WO | 2010/133473 | 11/2010 | | |
| WO | WO-2012062771 A1 * | 5/2012 | ............. | C11B 9/008 |
| WO | 2014/060345 | 4/2014 | | |

OTHER PUBLICATIONS

Dalko, P. I., "In the golden age of organocatalysis." Angewandte Chemie International Edition 43.39 (2004): 5138-5175.*
Allemann, C., "Theory of asymmetric organocatalysis of aldol and related reactions: Rationalizations and predictions." Accounts of chemical research 37.8 (2004): 558-569.*
International Search Report, dated Mar. 23, 2016.

* cited by examiner

*Primary Examiner* — John M Mauro
(74) *Attorney, Agent, or Firm* — Rankin, Hill & Clark LLP

(57) ABSTRACT

The present invention discloses a process for synthesis of chiral 2,4-disubstituted-tetrahydropyran-4-ol and its derivatives having a general formula (I) comprising of asymmetric reaction of an aliphatic aldehyde and a homoallylic alcohol in the presence of a chiral organocatalyst, and a fragrance and cosmetic composition containing chirally enriched molecules of the said general formula (I) prepared by the aforesaid process.

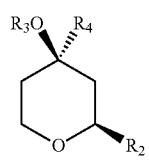

General Formula (I)

6 Claims, No Drawings

SYNTHESIS OF CHIRALLY ENRICHED 2,4-DISUBSTITUTED TETRAHYDROPYRAN-4-OL AND ITS DERIVATIVES

FIELD OF THE INVENTION

The present invention generally relates to the synthesis of chirally enriched 2,4-disubstituted tetrahydropyran-4-ol and its derivatives, using chiral organocatalyst.

BACKGROUND OF THE INVENTION

It is generally known that the Prins cyclization[1] of an aldehyde and a homoallylic alcohol provides a powerful access to tetrahydropyran-4-ols. Enantiomers/diastereomers of 2,4-disubstituted-tetrahydropyran-4-ol (a type of tetrahydropyran-4-ol) and its derivatives display different intensity of odor. Further, according to the prior art, the synthesis of enantiomers of 2,4-disubstituted-tetrahydropyran-4-ol and its derivatives require 5-7 synthetic steps.[2]

Numerous protonic acids and Lewis acids are known to catalyze Prins cyclization and excellent reviews have been published on the earlier work.[3, 4]
(1) Snider, B. B. In Comprehensive Organic Synthesis; Trost, B., Fleming, I., Heathcook, C. H., Eds.; Pergamon: New York, N.Y., 1991; Vol. 2, pp 527-561.
(2) Abate, A.; Brenna, E.; Fronza, G.; Fuganti, C.; Gatti, F. G.; Serra, S.; Zardoni, E. Helv. Chim. Acta 2004, 87, 765-780.
(3) Pastor, I. M.; Yus, M. Curr. Org. Chem. 2007, 11, 925-957.
(4) Olier, C.; Kaafarani, M.; Gastaldi, S.; Bertrand, M. P. Tetrahedron 2010, 66, 413-445.

However, the reactions as described in the prior publication at 2 above discloses a multi-step process for synthesis of chiral 2,4-disubstituted-tetrahydropyran-4-ol and its acetate derivative and hence results in a low yield of the final product. Also, the use of a chiral organocatalyst is not taught anywhere. On the contrary, they teach use of a biocatalyst during the reaction process which is more expensive and hence makes the process commercially unviable.

Further, recent patents WO2010/133473 A1, US 2011/0306779 A1 disclose a process for the preparation of 2-substituted-4-hydroxy-4-methyl-tetrahydropyran by treating isoprenol with an aldehyde and wherein the said reaction is carried out in the presence of water and strongly acidic cation exchanger, which are not chiral. Whereas patents US2014/0107352 A1 and WO 2014/060345 A1 relate to integrated preparation of 2-substituted 4-hydroxy-4-methyl-tetrahydropyrans and of 2-substituted-4-methyltetrahydropyran in the presence of acid catalysts such as hydrochloric or sulfuric acid but preferably methanesulfonic or p-toluenesulfonic acid or strongly acidic cation exchanger, followed by fractionation of reaction products and reduction of olefinic fraction by hydrogenation reaction.

However, the said prior art does not disclose the use of 1-(R) or 1-(S) camphor sulfonic acid as a chiral organocatalyst. Hence the present invention provides the synthesis of chirally enriched 2, 4-disubstituted-tetrahydropyran-4-ol, through the use of chiral organocatalyst, which is inexpensive, making the entire process commercially viable. Moreover, the organocatalyst described in the present invention yields enantiomerically enriched products in environmentally benign conditions, which is why it is also termed as green process.

OBJECT OF THE INVENTION

The objective of the present invention is to provide a single step process for the synthesis of chirally enriched 2,4-disubstituted tetrahydropyran-4-ol and its derivatives, by the use of an organocatalyst which is less expensive, making the entire process commercially viable.

Another objective of this invention is to find a process for the synthesis of chirally enriched 2,4-disubstituted tetrahydropyran-4-ol and its derivatives that can lead to a finished product that is already enantiomerically and/or diastereomerically pure or at least substantially enriched in the desired chiral molecules.

Yet another object of the present invention is the synthesis of chiral molecules of general formula (I) and/or its isomers which exhibit fresh, soft, sweet and natural floral odor reminiscent of muguet with some rose oxide side note and earthy nuances that resembles natural odors.

Yet another object of the present invention is to synthesize chirally enriched compounds which exhibit increased bioactivity intensity which results in a corresponding increase in persistence of the aroma given off by the perfumery composition and therefore facilitates the said perfumery composition to have a decreased concentration of the odorant that provides a longer lasting aroma as compared to conventional perfumery composition. Therefore, the safety for human use is increased.

SUMMARY OF THE INVENTION

The present invention eliminates or substantially alleviates the disadvantages and shortcomings in the prior art methods.

Typically, the present invention teaches "A process for synthesis of chiral 2,4-disubstituted-tetrahydropyran-4-ol and its derivatives having a general formal (I)

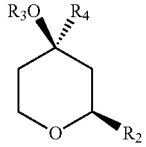

General Formula (I)

comprising of asymmetric reaction of an aliphatic aldehyde and a homoallylic alcohol in the presence of a chiral organocatalyst."

Typically, a process for synthesis of chiral acyl derivatives of 2,4-disubstituted-tetrahydropyran-4-ol and its derivatives having a general formal (I) in the presence of a chiral organocatalyst as described above which uses an additional reagent acyl anhydride.

Typically, a process for synthesis of chiral 2,4-disubstituted-tetrahydropyran-4-ol and its derivatives having a general formal (I) in the presence of a chiral organocatalyst as described above, wherein the said general formula (I) has substituents R1, R2, R3 and R4 which are selected from the group consisting of hydrogen, methyl, ethyl, propyl, butyl, isopropyl, isobutyl, isobutenyl, acetyl, propionoyl or similar groups.

Typically, the said chiral organocatalyst is 1-(R)-camphor-sulphonic acid or 1-(S)-camphor-sulphonic acid.

Typically, a fragrance composition containing chirally enriched molecules of the said general formula (I) prepared by the process described above which comprises at least one perfume and/or at least one cologne and/or at least one eau du toilette and/or at least one eau du parfum and/or at least one cosmetic and/or at least one personal care product and/or at least one cleansing product and/or at least one fabric softener and/or at least one air freshener.

Typically, a cosmetic composition containing an olfactory acceptable amount of chirally enriched molecules of the said general formula (I) prepared by the process as described above.

DETAILED DESCRIPTION

A process that satisfies the above requirements is achieved in extremely simple but no less advantageous manner. The foregoing needs are met, to a great extent, by the present invention, which describes synthesis of chirally enriched odorous 2,4-disubstituted tetrahydropyran-4-ol and its derivatives, that are obtained using chiral organocatalyst, having increased floral odour.

An embodiment of the present invention pertains to synthesis of molecules of general formula (I) and/or its isomers (Figure 1). Figure 2 shows the three examples—Type A, Type B, and Type C of the said general formula (I).

FIG. 1

General Formula (I)

FIG. 2

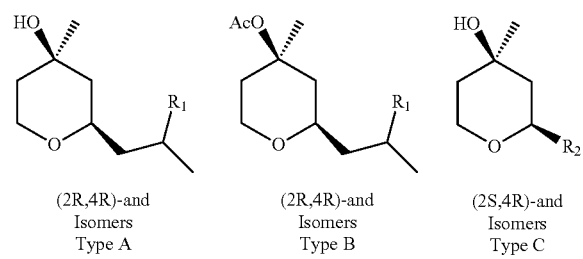

(2R,4R)- and Isomers Type A (2R,4R)- and Isomers Type B (2S,4R)- and Isomers Type C Yet another embodiment of the present invention pertains to a process of synthesizing the compound of general formula (I) and/or its isomers by using a chiral organocatalyst.

Yet another embodiment of the present invention pertains to a process of synthesizing the compound of general formula (I) and/or its isomers wherein the chiral organocatalyst used is preferably metal free.

An embodiment of the present invention pertains to molecules of general formula (I) and/or its isomers (Figures 1 and 2), wherein substituents $R_1$, $R_2$, $R_3$ and $R_4$ are selected from the group consisting of hydrogen, methyl, ethyl, propyl, butyl, acetyl, propanol, isobutyl, isopropyl, isobutyl or similar groups.

In a preferable embodiment of the present invention, chiral organocatalyst is chiral sulfonic acid for example (+)-camphor-sulphonic acids or (−)-camphor-sulphonic acids.

The present invention further pertains to the asymmetric synthesis of chiral compounds using other related catalysts such as menthone sulfonic acid or chiral phosphoric acid e.g. modified (+)- or (−)-2,2'-Binaphthol (BINOL)-phosphoric acid.

The present invention pertains to a method of synthesizing enantiomerically and/or diastereomerically enriched molecules (chirally enriched) of general formula (I).

The invention also teaches a fragrance/perfumery composition comprising of chirally enriched molecules synthesized according to the above mentioned process and at least one perfume and/or a cologne and/or an eau du toilette and/or an eau du parfum and/or a cosmetic and/or a personal care products and/or a cleansing products and/or a fabric softener and/or an air freshener.

The present invention also pertains, to a cosmetic composition comprising an olfactory acceptable amount of the chirally enriched compound prepared according to the abovementioned invented process. Chirally enriched compounds with a general formula (I) are claimed for perfumery, cosmetic and agrochemical applications. Compounds with general formula (I) obtained in this method are further used to synthesize chirally enriched 2,4-disubstituted-tetrahydro-2H-pyrans.

Yet another embodiment of the present invention pertains to a process of making a perfumery composition including mixing the chirally enriched compound of general formula (I) and/or its isomers synthesized using the said process with at least one ingredient selected from the group consisting of solvents, carriers, stabilizers, emulsifiers, moisturizers, dispersants, diluents, thickeners, thinners, other odorants and adjuvants.

Yet another embodiment of the present invention relates to a process of using chirally enriched compound of general formula (I) and/or its isomers synthesized using the said process for making an agrochemical composition, with at least one ingredient selected from the group consisting of solvents, carriers, stabilizers, emulsifiers, moisturizers, dispersants, diluents, thickeners, thinners and other adjuvants acceptable in an agrochemical composition.

There has thus been outlined, rather broadly, certain embodiments of the invention in order that the detailed description thereof may be better understood herein, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in their application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting the invention.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions in so far as they do not depart from the spirit and scope of the present invention.

Figures 3, 4, and 5 show examples of chiral 2,4-disubstituted tetrahydropyrans of types A, B, and C respectively shown in Figure 2.

FIG. 3: Some examples of chiral 2,4-disubstituted tetrahydropyrans (type A) of present invention.

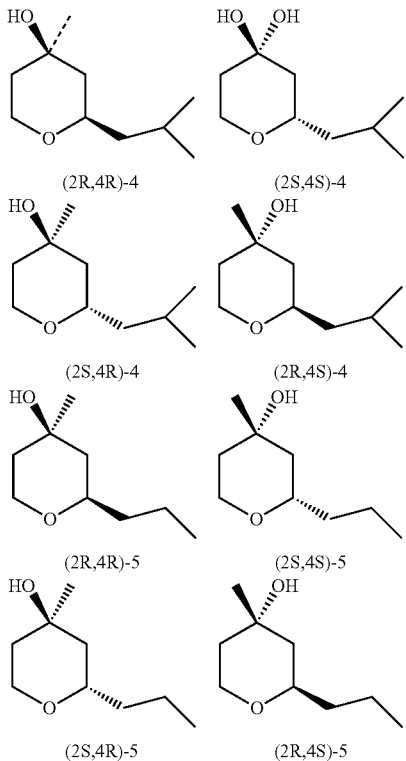

FIG. 4: Some examples of chiral 2,4-disubstituted tetrahydropyrans (type B) of present invention.

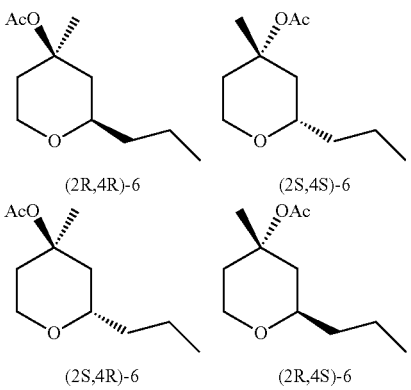

FIG. 5: Some examples of chiral 2,4-disubstituted tetrahydropyrans (type C) of present invention.

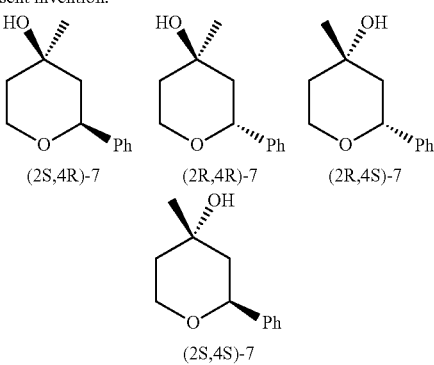

It is an advantage of one or more of the embodiments of the present invention that the chirally enriched compounds of present invention exhibit increased bioactivity as compared to the racemic molecules obtained by conventional synthesis.

Due to this increased bioactivity, less amount of enantiomerically enriched compounds of general formula (I) and/or its isomers is required in perfumery or agrochemical compositions thereof.

In addition, this increased bioactivity intensity results in a corresponding increase in persistence of the aroma given off by the perfumery compositions and therefore facilitates the said perfumery compositions to have a decreased concentration of the odorant that provides a longer lasting aroma as compared to conventional perfumery compositions. Therefore, the safety for human use is increased.

In Figures titled SCHEME 1 to 8 below are shown compounds of general formula (I) and/or its isomers obtained by a reaction of a homoallylic alcohol derivative (2) with an aldehyde (3a-c) in the presence of chiral organocatalyst such as (+)-camphor sulphonic acid or (−)-camphor sulphonic acid (1, CSA) wherein:

SCHEME 1 shows Synthesis of (2R,4R)-4 and (2S,4R)-4
SCHEME 2 shows Synthesis of (2S,4S)-4 and (2R,4S)-4
SCHEME 3 shows Synthesis of (2R,4R)-5 and (2S,4R)-5
SCHEME 4 shows Synthesis of (2S,4S)-5 and (2R,4S)-5
SCHEME 5 shows Synthesis of (2R,4R)-6 and (2S,4R)-6
SCHEME 6 shows Synthesis of (2S,4S)-6 and (2R,4S)-6
SCHEME 7 shows Synthesis of (2S,4R)-7 and (2R,4R)-7
SCHEME 8 shows Synthesis of (2R,4S)-7 and (2S,4S)-7

SCHEME 1

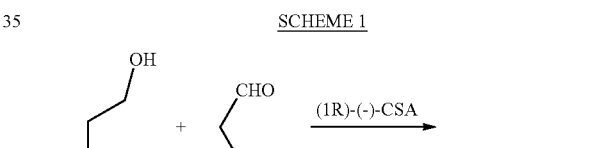

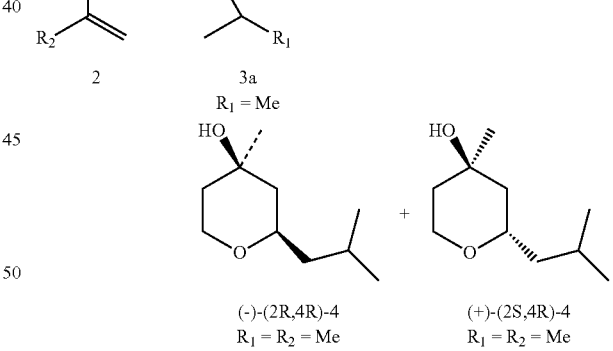

SCHEME 2

-continued
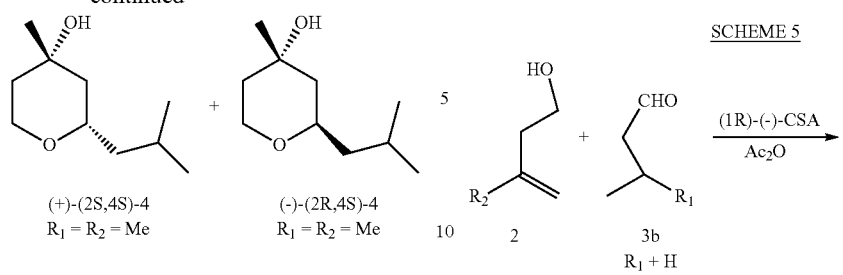
SCHEME 3
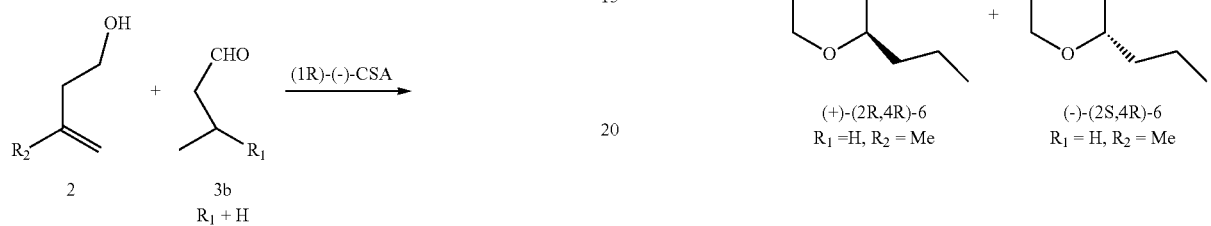
SCHEME 4
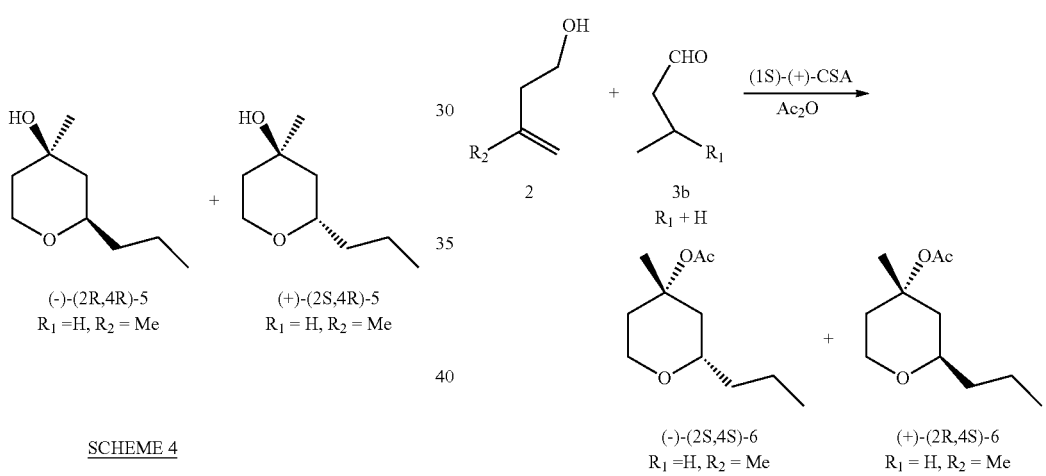
SCHEME 5
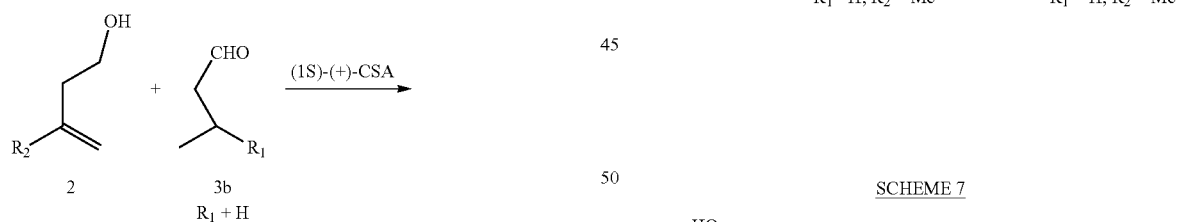
SCHEME 6
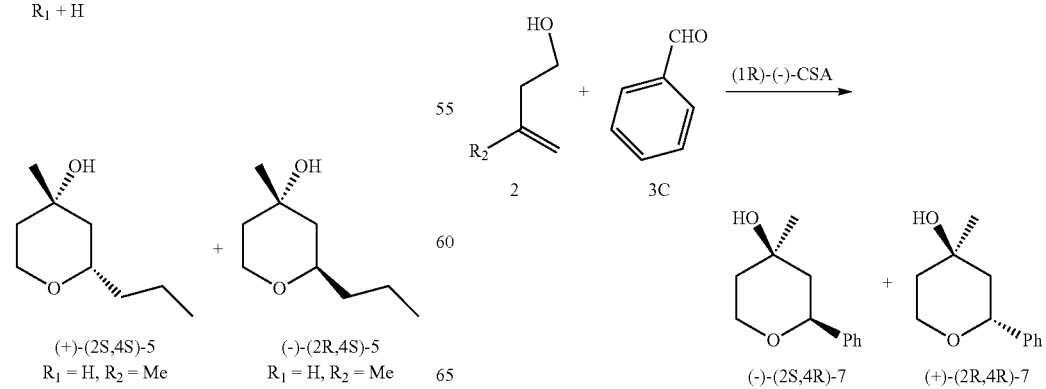
SCHEME 7

SCHEME 8

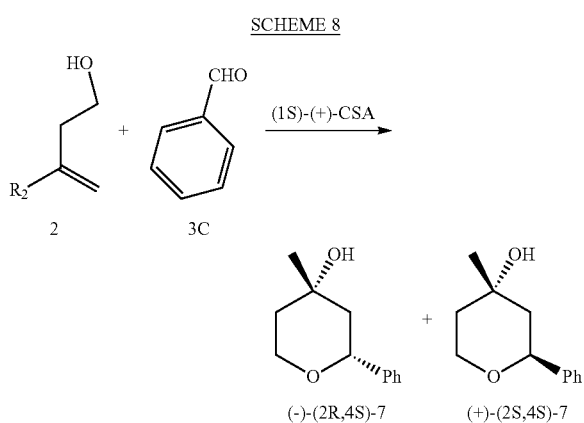

The process according to the present invention will now be described in greater detail in the following Examples:

Example 1

(2R,4R) and (2S,4R)-2-Isobutyl-4-methyltetrahydro-2H-pyran-4-ol, 4: (Scheme 1)

In a 3 necked flask a mixture of graphite (1.5 g), isoprenol (2, 20 g, 0.232 mol), (−)-camphor sulfonic acid (CSA) (1.5 g, 0.0064 mol) and isovaleraldehyde (3, 20 g, 0.232 mol) were added with stirring. The stirring was continued for 4 h at RT. The reaction mixture was filtered. The filtrate was neutralized and the organic layer was dried over anhydrous $Na_2SO_4$ and the solvent was removed in vacuum. The residue was subjected to column chromatography to give the hydroxyl compounds (2S, 4R)-4 ($R_1$=Me, $R_2$=H) and (2R, 4R)-4 ($R_1$=Me, $R_2$=H) (28 g, 70%).

Data for (2S,4R)-4
$[\alpha]^{20}_D$=+1.23 (c=0.72, $CHCl_3$);
IR: $cm^{-1}$ 3427, 2957, 2870, 1467, 1371, 1274, 1170, 1109, 985, 889, 797.
$^1$H-NMR (400 MHz): δ 3.80 (ddd, J=11.5, 5.5, 1.8, 1H), 3.77 (ddd, J=12.5, 11.5, 2.4, 1H), 3.69 (dddd, J=11.1, 8.4, 4.4, 2.2, 1H), 1.82-1.74 (m, 1H), 1.64 (ddd, J=13.6, 12.5, 5.5, 1H), 1.50 (dt, J=13.6, 2.4, 1H), 1.48-1.41 (m, 1H), 1.30 (dd, J=13.6, 11.1, 1H), 1.25 (s, 3H), 1.13 (ddd, J=13.3, 8.3, 4.5, 1H), 0.90 (d, J=6.6, 6H).
$^{13}$C-NMR: δ 71.2, 68.0, 63.6, 45.5, 45.2, 38.8, 31.8, 24.4, 23.4, 22.5.
GC/MS: (m/z) 172, 154, 139, 115, 97, 87, 69, 58, 43.
Data for (2R,4R)-4
$[\alpha]^{20}_D$=−4.87 (c=1.09, $CHCl_3$);
IR: $cm^{-1}$ 3400, 2956, 2868, 1651, 1468, 1378, 1169, 1112, 891, 638;
$^1$H-NMR (400 MHz): δ 3.95 (ddd, J=12.0, 5.4, 2.0, 1H), 3.42 (ddd, J=12.5, 11.9, 2.4, 1H), 3.35 (ddd, J=11.2, 8.2, 4.4, 2.3, 1H), 1.82-1.72 (m, 1H), 1.69 (dddq, J=12.7, 12.5, 5.4, 0.8, 1H), 1.62 (dt, J=12.5, 2.4, 1H), 1.58 (dddd, J=12.6, 2.4, 2.3, 2.0, 1H), 1.49 (ddd, J=13.9, 8.3, 5.9, 1H), 1.35 (ddq, J=12.5, 11.5, 0.8, 1H), 1.3 (t, J=0.8, 3H), 1.18 (ddd, J=13.9, 8.3, 4.5, 1H), 0.90 (d, J=6.6, 6H);
$^{13}$C-NMR: δ 73.6, 68.7, 65.4, 46.9, 45.5, 40.6, 25.4, 24.3, 23.2, 22.4;
GC/MS: (m/z): 172, 154, 139, 115, 97, 87, 71, 58, 43.

Example 2 (Alternative Procedure for Scheme 1)

A mixture of (−)-camphor-10-sulphonic acid (1, 1.5 g, 0.0064 mol), graphite (1.5 g), isoprenol (2, 20 g, 0.232 mol) and isovaleraldehyde (3, 20 g, 0.232 mol) was stirred at 50° C. for 4 h. The reaction mixture was subjected to usual workup and purification by column chromatography to yield (2R,4R)-4 and (2S,4R)-4, (26 g, 65%).

Example 3

(2R,4S) and (2S,4S)-2-Isobutyl-4-methyltetrahydro-2H-pyran-4-ol, 4: (Scheme 2)

A mixture of (+)-camphor-10-sulphonic acid (1, 1.5 g, 0.0064 mol), graphite (1.5 g), isoprenol (2, 20 g, 0.232 mol) and isovaleraldehyde (3a 20 g, 0.232 mol) was stirred at RT for 4 h. The products were isolated by filtration. The filtrate was neutralized, the organic layer was dried over anhydrous $Na_2SO_4$ and the solvent was removed in vacuum. The residue was subjected to column chromatography to give the hydroxyl compounds (2S,4S)-4 and (2R,4S)-4 (27.2 g, 68%).

Data for (2R,4S)-4:
$[\alpha]^{20}_D$=−0.96 (c=1.09, $CHCl_3$);
IR: $cm^{-1}$ 3400, 2956, 2868, 1651, 1468, 1378, 1169, 1085, 961, 771;
$^1$H-NMR (400 MHz): δ 3.80 (ddd, J=11.5, 5.5, 1.8, 1H), 3.77 (ddd, J=12.5, 11.5, 2.4, 1H), 3.69 (dddd, J=11.1, 8.4, 4.4, 2.2, 1H), 1.82-1.74 (m, 1H), 1.64 (ddd, J=13.6, 12.5, 5.5, 1H), 1.50 (dt, J=13.6, 2.4, 1H), 1.48-1.41 (m, 1H), 1.30 (dd, J=13.6, 11.1, 1H), 1.25 (s, 3H), 1.13 (ddd, J=13.3, 8.3, 4.5, 1H), 0.90 (d, J=6.6, 6H).
$^{13}$C-NMR: δ 71.2, 67.9, 63.6, 45.5, 45.2, 38.8, 31.8, 24.3, 23.4, 22.4;
GC/MS: (m/z) 172, 154, 139, 115, 97, 87, 69, 58, 43.
Data for (2S,4S)-4:
$[\alpha]^{20}_D$=+4.57 (c=1.04, $CHCl_3$)
IR: $cm^{-1}$ 3391, 2956, 2868, 1652, 1468, 1378, 1250, 1169, 1084, 919, 756, 638.
$^1$H-NMR (400 MHz): δ 3.95 (ddd, J=12.0, 5.4, 2.0, 1H), 3.42 (ddd, J=12.5, 11.9, 2.4, 1H), 3.35 (ddd, J=11.2, 8.2, 4.4, 2.3, 1H), 1.82-1.72 (m, 1H), 1.69 (dddq, J=12.7, 12.5, 5.4, 0.8, 1H), 1.62 (dt, J=12.5, 2.4, 1H), 1.58 (dddd, J=12.6, 2.4, 2.3, 2.0, 1H), 1.49 (ddd, J=13.9, 8.3, 5.9, 1H), 1.35 (ddq, J=12.5, 11.5, 0.8, 1H), 1.3 (t, J=0.8, 3H), 1.18 (ddd, J=3.9, 8.3, 4.5, 1H), 0.90 (d, J=6.6, 6H).
$^{13}$C-NMR: δ 73.6, 68.8, 65.4, 47.1, 45.5, 40.6, 25.4, 24.4, 23.2, 22.4.
GC/MS (m/z): 172, 154, 139, 115, 97, 87, 71, 58, 43.

Example 4 (Alternative Procedure for Scheme 2)

In 3 necked flask a mixture of graphite (15 g), isoprenol (2, 20 g, 2.32 mol), (+)-camphor sulfonic acid (1, 15 g, 0.064 mol) and isovaleraldehyde (3, 20. g, 2.32 mol) were added. The stirring was continued for 4 h at RT, The reaction mixture was filtered. The filtrate was neutralized and was subjected to fractional distillation in vacuum to give the hydroxyl compounds (2R,4S)-4 and (2S,4S)-4, (25 g, 62.5%).

Example 5 (Alternative Procedure for Scheme 2)

A mixture of (+)-camphor-10-sulphonic acid (1, 1.5 g, 0.0064 mol), graphite (1.5 g), isoprenol (2, 20 g, 0.232 mol) and isovaleraldehyde (3, 20 g, 0.232 mol) was stirred at 50° C. for 4 h. The products were isolated by filtration. The filtrate was neutralized and subjected to purification by column chromatography to yield (2R,4S)-4 and (2S,4S)-4, (24 g, 60%).

Example 6

(2R,4R) and (2S,4R)-2-Propyl-4-methyltetrahydro-2H-pyran-4-ol, 5 (Scheme 3)

In 3 necked a mixture of graphite (1.5 g), isoprenol (2, 20 g, 0.232 mol) was stirred for 2 min. and (−)-camphor sulfonic acid (1, 1.5 g, 0.0064 mol) and butyraldehyde (3b, 16.7 g, 0.232 mol) were added. The stirring was continued for 4 h at RT, The reaction mixture was filtered. The filtrate was neutralized and was subjected to column chromatography to give the hydroxyl derivative (2S,4R)-5 and (2R,4R)-5 (24.8 g, 62%).

Data for (2S,4R)-5:
$[\alpha]^{20}_D$+0.86 (c=0.86, CHCl$_3$);
IR: cm$^{-1}$ 3417, 2960, 2872, 1459, 1380, 1269, 1174, 1106, 1003, 755;
$^1$H-NMR (400 MHz): δ 3.90-3.80 (m, 1H), 3.79-3.72 (m, 1H), 3.65-3.56 (m, 1H), 1.75-1.18 (m, 8H), 1.26 (s, 3H), 0.92 (t, J=7.0, 3H);
$^{13}$C-NMR: δ 72.8, 67.9, 63.7, 44.7, 38.8, 38.4, 31.8, 18.7, 14.2;
GC/MS (m/z): 157, 140, 125, 112, 97, 84, 69, 55, 43.

Data for (2R,4R)-5
$[\alpha]^{20}_D$=−4.60 (c=1.09, CHCl$_3$)
IR: cm$^{-1}$ 3400, 2956, 2868, 1651, 1468, 1378, 1169, 1112, 891, 638;
$^1$H-NMR (400 MHz): δ 3.95 (ddd, J=12.0, 0.4, 2.0, 1H), 3.42 (ddd, J=12.5, 11.9, 2.4, 1H), 3.35 (ddd, J=11.2, 8.2, 4.4, 2.3, 1H), 1.82-1.72 (m, 1H), 1.69 (dddq, J=12.7, 12.5, 5.4, 0.8, 1H), 1.62 (dt, J=12.5, 2.4, 1H), 1.58 (dddd, J=12.6, 2.4, 2.3, 2.0, 1H), 1.49 (ddd, J=13.9, 8.3, 5.9, 1H), 1.35 (ddq, J=12.5, 11.5, 0.8, 1H), 1.3 (t, J=0.8, 3H), 1.18 (ddd, J=13.9, 8.3, 4.5, 1H), 0.90 (d, J=6.6, 6H);
$^{13}$C-NMR: δ 73.6, 68.7, 65.4, 46.9, 45.5, 40.6, 25.4, 24.3, 23.2, 22.4;
GC/MS (m/z): 172, 154, 139, 115, 97, 87, 71, 58, 43.

Example 7

(2R,4S) and (2S,4S)-2-Isobutyl-4-methyltetrahydro-2H-pyran-4-ol, 5 (Scheme 4)

In 3 necked a mixture of graphite (1.5 g), isoprenol (2, 20 g, 0.232 mol) was stirred for 2 min. and (+)-camphor sulfonic acid (1, 1.5 g, 0.0064 mol) and butyraldehyde (3b, 0.0167 kg, 0.232 mol) were added. The stirring was continued for 4 h at RT, The reaction mixture was filtered. The filtrate was neutralized and was subjected to column chromatography to give the hydroxyl derivative (2R,4S)-5 and (2S,4S)-5 (24.8 g, 62%).

Data for (2R,4S)-5
$[\alpha]^{20}_D$=−0.76 (c=0.75, CHCl$_3$);
IR cm$^{-1}$: 3420, 2960, 2872, 1459, 1380, 1269, 1174, 1105, 1003, 809, 755;
$^1$H-NMR (400 MHz): δ 3.90-3.80 (m, 1H), 3.79-3.72 (m, 1H), 3.65-3.56 (m, 1H), 1.75-1.18 (m, 8H), 1.26 (s, 3H), 0.92 (t, J=7.0, 3H);
$^{13}$C-NMR: δ 72.8, 67.9, 63.7, 44.7, 38.8, 38.4, 31.8, 18.7, 14.2;
GC/MS (m/z): 157, 140, 125, 112, 97, 84, 69, 55, 43.

Data for (2S,4S)-5
$[\alpha]^{20}_D$=+5.21, (c=0.48, CHCl$_3$);
IR cm$^{-1}$: 3401, 2960, 2871, 1465, 1378, 1265, 1172, 1109, 1003, 891, 810, 755;
$^1$H-NMR (400 MHz): δ 3.96 (ddd, J=12.0, 5.2, 1.8, 1H), 3.43 (dt, J=2.6, 12.0, 1H), 3.33-3.27 (m, 1H), 1.74-1.34 (m, 8H), 1.33 (s, 3H), 0.91 (t, J=7.1, 3H);
$^{13}$C-NMR: δ 75.3, 68.8, 65.4, 46.6, 40.6, 38.5, 25.4, 18.7, 14.1;
GC/MS (m/z): 157, 140, 125, 115, 103, 97, 87, 71, 58, 43.

Example 8

(2R,4R) and (2S,4R)-2-Propyl-4-acetoxy-4-methyl-tetrahydro-2H-pyran, 6 (Scheme 5)

In a 3-necked flask a mixture of graphite (1.5 g), isoprenol (2, 20 g, 0.232 mol) was stirred for 2 min. and (−)-camphor sulfonic acid (1, 1.5 g, 0.0064 mol) and butyraldehyde (3, 16.7 g, 0.232 mol) were added. The stirring was continued for 2 h at RT and acetic anhydride (0.047 L, 0.497 mol) was added and stirring continued for 4 h. The reaction mixture was filtered. The filtrate was neutralized, the organic layer was dried over anhydrous Na$_2$SO$_4$ and the solvent was removed in vacuum. The residue was subjected to column chromatography to give the acetoxy derivative (2S,4R)-6 and (2R,4R)-6, (29.5 g, 67%).

Data for (2S,4R)-6
$[\alpha]^{20}_D$=−3.12 (c=0.94, CHCl$_3$)
IR cm$^{-1}$: 2960, 2933, 1733, 1462, 1367, 1242, 1145, 1019, 939, 806, 757.
$^1$H-NMR (400 MHz): δ 3.82 (ddd, J=11.6, 5.3, 1.6, 1H), 3.61 (ddd, J=12.6, 11.6, 2.1, 1H), 3.47 (dddd, J=11.4, 7.4, 4.6, 2.3, 1H), 2.24 (dt, J=13.8, 2.3, 1H), 2.18 (dddd, J=14.1, 2.3, 2.1, 1.6, 1H), 2.03 (s, 3H), 1.50 (s, 3H), 1.58-1.30 (m, 41-1), 1.34 (ddd, J=14.1, 12.6, 5.3, 1H), 1.20 (dd, J=13.8, 11.3, 1H), 0.91 (t, 3H).
$^{13}$C-NMR: δ 170.5, 79.4, 72.6, 63.5, 42.2, 38.3, 36.4, 26.3, 22.4, 18.7, 14.2.
GC/MS (m/z): 201, 185, 157, 140, 125, 115, 97, 87, 71, 58, 43.

Data for (2R,4R)-6
$[\alpha]^{20}_D$=+1.72 (c=2.08, CHCl$_3$);
IR cm$^{-1}$: 2960, 2871, 1732, 1466, 1377, 1251, 1106, 1021, 931, 811, 758.
$^1$H-NMR (400 MHz): δ 3.93 (ddd, J=12.1, 5.3, 1.9, 1H), 3.47 (ddd, J=12.6, 12.1, 2.3, 1H), 3.34 (m, 1H), 2.11 (dt, J=12.6, 2.2, 1H), 2.04 (dddd, J=12.8, 2.3, 2.2, 1.9, 1H), 1.93 (s, 3H), 1.86 (dddq, J=12.8, 12.6, 5.3, 0.9, 1H), 1.62 (s, 3H), 1.57-1.30 (m, 4H), 1.54 (ddq, J=12.6, 11.5, 0.9, 1H), 0.91 (t, J=7.2, 3H).
$^{13}$C-NMR: δ 170.3, 80.1, 74.3, 64.6, 43.5, 38.4, 37.7, 22.5, 21.7, 18.7, 14.1.
GC/MS (m/z): 201, 185, 170, 157, 140, 125, 112, 97, 86, 69, 55, 43.

Example 9

(2R,4S) and (2S,4S)-2-Propyl-4-acetoxy-4-methyl-tetrahydro-2H-pyran, 6 (Scheme 6)

In a 3-necked a mixture of graphite (1.5 g), isoprenol (2, 20 g, 0.232 mol) was stirred for 2 min. and (+)-camphor sulfonic acid (1, 1.5 g, 0.0064 mol) and butyraldehyde (3, 16.7 g, 0.232 mol) were added. The stirring was continued for 2 h at RT and acetic anhydride (0.047 L, 0.497 mol) was added and stirring continued for 3 h. The reaction mixture was filtered. The filtrate was neutralized by addition of saturated NaHCO$_3$ and extracted with ethyl acetate. The organic layer was dried and filtered. The solvent was removed from organic layer and the residue was subjected to column chromatography to give the acetate (2R,4S)-6 (R$_1$=Me, R$_2$=H) and (2S,4S)-6 (R$_1$=Me, R$_2$=H), (31.24 g, 71%).

Data for (2R,4S)-6
[α]$^{20}_D$=+3.62 (c=0.43, CHCl$_3$);
IR cm$^{-1}$: 2960, 2871, 1736, 1461, 1369, 1242, 1110, 107, 807, 756.
$^1$H-NMR (400 MHz): δ 3.82 (ddd, J=11.6, 5.3, 1.6, 1H), 3.61 (ddd, J=12.6, 11.6, 2.1, 1H), 3.47 (dddd, J=11.4, 7.4, 4.6, 2.3, 1H), 2.24 (dt, J=13.8, 2.3, 1H), 2.18 (dddd, J=14.1, 2.3, 2.1, 1.6, 1H), 2.03 (s, 3H), 1.50 (s, 3H), 1.58-1.30 (m, 4H), 1.34 (ddd, J=14.1, 12.6, 5.3, 1H), 1.20 (dd, J=13.8, 11.3, 1H), 0.91 (t, 3H).
$^{13}$C-NMR: δ 170.5, 79.4, 72.6, 63.5, 42.2, 38.3, 36.4, 26.3, 22.5, 18.7, 14.2
GC/MS (m/z): 201, 182, 157, 140, 125, 112, 97, 84, 69, 55, 43.

Data for (2S, 4S)-6:
[α]$^{20}_D$=-1.62 (c=1.36, CHCl$_3$);
IR cm$^{-1}$: 2960, 2871, 1732, 1467, 1369, 1251, 1128, 1021, 949, 931, 811, 757.
$^1$H-NMR (400 MHz) δ: 3.93 (ddd, J=12.1, 5.3, 1.9, 1H), 3.47 (ddd, J=12.6, 12.1, 2.3, 1H), 3.34 (m, 1H), 2.11 (dt, J=12.6, 2.2, 1H), 2.04 (dddd, J=12.8, 2.3, 2.2, 1.9, 1H), 1.93 (s, 3H), 1.86 (dddq, J=12.8, 12.6, 5.3, 0.9, 1H), 1.62 (s, 3H), 1.57-1.30 (m, 4H), 1.54 (ddq, J=12.6, 11.5, 0.9, 1H), 0.91 (t, J=7.2, 3H).
$^{13}$C-NMR: δ 170.3, 80.1, 74.3, 64.6, 43.5, 38.4, 37.7, 22.5, 21.7, 18.7, 14.1.
GC/MS (m/z): 201, 185, 157, 140, 125, 112, 97, 69, 55, 43.

Example 10 (Alternative Procedure for Scheme 6)

A mixture of (−)-camphor-10-sulphonic acid (1, 15 g, 0.064 mol), graphite (15 g), isoprenol (2, 0.2 kg, 2.32 mol) and butyraldehyde (3, 0.167 kg, 2.31 mol) was stirred at 50° C. for 2 h and acetic anhydride (0.47 L, 4.97 mol) was added and stirring continues for 3 h. The products were isolated by filtration. The filtrate was neutralized by sat. NaHCO$_3$, the organic layer was dried on anhydrous Na$_2$SO$_4$, filtered and subjected to purification by fractional distillation in vacuum to yield (2S,4R)-6 and (2R,4R)-6, (31.7 g, 72%).

Example 11 (Alternative Procedure for Scheme 6)

A mixture of (+)-camphor-10-sulphonic acid (1, 15 g, 0.064 mol), graphite (15 g), isoprenol (0.2 kg, 2.32 mol) and butyraldehyde (0.167 kg, 2.32 mol) was stirred for 2 h at RT and acetic anhydride (0.47 L, 4.97 mol) was added and stirring was continued for 3 h at 50° C. The products were isolated by filtration. The filtrate was subjected to purification by distillation in vacuum to yield (2S,4S)-6 and (2R, 4S)-6, (33.4 g, 76%).

Example 12

(2R,4R) and (2S,4R)-2-Phenyl-4-methyltetrahydro-2H-pyran-4-ol, 7 (Scheme 7)

A mixture of (−)-camphor-10-sulphonic acid (1, 1.5 g, 0.0064 mol), graphite (1.5 g), isoprenol (2, 20 g, 0.232 mol) and benzaldehyde (3c, 24.6 g, 0.232 mol) was stirred at RT for 4 h. The products were isolated by filtration. The filtrate was subjected to purification by column chromatography to yield hydroxyl derivative (2S,4R)-7 and (2S,4S)-7, (22.42 g, 56.0%).

Data for anti-(2R,4R)-7, [α]$_D$=−16.43. (c=1.33, CHCl$_3$).
IR (neat) cm$^{-1}$: 3401, 2942, 2858, 1495, 1377, 1252, 1091, 942, 766.
$^1$H-NMR (400 MHz): δ 7.37-7.23 (m, 5H), 4.71 (dd, J=2.6, 11.7, 1H), 4.03-3.94 (m, 2H), 1.84-1.77 (m, 2H), 1.66 (dd, 11.7, 13.7, 1H), 1.54-1.46 (m, 2H), 1.31 (s, 3H).
$^{13}$C-NMR: δ 142.8, 128.5, 128.5, 127.5, 126.0, 126.0, 75.4, 68.2, 64.2, 46.7, 38.6, 31.9.
GC/MS (m/z): 191, 174, 159, 145, 131, 121, 105, 91, 77, 71, 65, 58, 51, 43.

Data for syn-(2S,4R)-7, [α]$_D$=+8.42 (c=0.78, CHCl$_3$).
IR (neat) cm$^{-1}$: 3399, 2943, 2859, 1495, 1377, 1252, 1092, 942, 764.
$^1$H-NMR (400 MHz): δ 7.40-7.20 (m, 5H), 4.37 (d, J=11.7, 1H), 4.12 (dd, J=3.95, 12.1, 1H), 3.62 (t, J=11.15, 1H), 1.88 (dt, 12.6, 2.6, 1H), 1.92-1.81 (m, 2H), 1.70 (dq, 12.7, 2.4, 1H), 1.45 (s, 3H).
$^{13}$C-NMR: δ 142.2, 128.6, 128.6, 127.8, 126.1, 126.1, 77.8, 69.3, 66.1, 48.5, 40.5, 25.5.
GC/MS (m/z): 191, 174, 159, 145, 131, 121, 105, 91, 77, 71, 65, 58, 51, 43.

Example 13

(2R,4S) and (2S,4S)-2-Phenyl-4-methyltetrahydro-2H-pyran-4-ol, 7 (Scheme 8): A mixture of (+)-camphor-10-sulphonic acid (1, 1.5 g, 0.0064 mol), graphite (1.5 g), isoprenol (2, 20 g, 0.232 mol) and benzaldehyde (3c, 24.6 g, 0.232 mol) was stirred at RT for 4 h. The products were isolated by filtration. The filtrate was neutralized by sat. NaHCO$_3$, the organic layer was dried on Anh.Na$_2$SO$_4$, filtered and subjected to purification by column chromatography over silica gel to yield hydroxyl derivative (2S,4S)-7, (2R,4S)-7, (26.2 g, 58.7%).

Example 14 (Alternative Procedure for Scheme 8)

A mixture of (−)-camphor-10-sulphonic acid (1, 20 g, 0.085 mol), graphite (40 g), isoprenol (2, 200 g, 23.2 mol) and benzaldehyde (3c, 246 g, 23.2 mol) was stirred at RT for 3 h. The products were isolated by filtration. The filtrate was neutralized by sat. NaHCO$_3$, the organic layer was dried on Anh. Na$_2$SO$_4$, filtered and subjected to purification by to fractional vacuum distillation to yield hydroxyl derivative (2S,4R)-7, CHCl$_3$) and (2R,4R)-7, (250 g, 56%).

Some Advantages

It is an advantage of one or more of the embodiments of the present invention that the chirally enriched 2,4-disubstituted tetrahydropyran-4-ol and its derivatives synthesized by the process claimed in the present invention exhibit increased bioactivity as compared to the racemic molecules obtained by conventional synthesis.

Due to the said increased bioactivity, the fewer amounts of an chirally enriched compound of general formula (I) and/or its isomers is required in perfumery or agrochemical compositions thereof.

The said increased bioactivity intensity results in a corresponding increase in persistence of the aroma given off by the perfumery compositions and therefore facilitates perfumery compositions having a decreased concentration of the odorant which in turn provides a long lasting aroma as compared to conventional perfumery compositions. Therefore, the safety for human use is increased.

Many features and advantages of the present invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

We claim:

1. A process for synthesis of chirally enriched 2,4-disubstituted-tetrahydropyran-4-ol and its derivatives having a general formula (I)

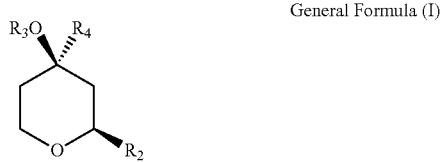

General Formula (I)

comprising a reaction of an aliphatic aldehyde and a homoallylic alcohol in the presence of a chiral organocatalyst;
wherein R2, R3 and R4 are selected from the groups consisting of hydrogen, methyl, ethyl, propyl, butyl, isopropyl, isobutyl, isobutenyl, acetyl or propionoyl;
wherein the chiral organocatalyst is 1-(R)-camphor-sulphonic acid or 1-(S)-camphor-sulphonic acid.

2. The process according to claim 1, wherein after the reaction of the aliphatic aldehyde and the homoallylic alcohol in the presence of the chiral organocatalyst, acyl anhydride is added thereto.

3. A fragrance composition containing chirally enriched molecules of the general formula (I) prepared by the process as claimed in claim 1 with at least one perfume and/or at least one cologne and/or at least one eau du toilette and/or at least one eau du parfum and/or at least one cosmetic and/or at least one personal care product and/or at least one cleansing product and/or at least one fabric softener and/or at least one air freshener,
wherein the fragrance composition is enriched with (2R, 4R) isomer of 2,4-disubstituted-tetrahydropyran-4-ol.

4. A cosmetic composition containing an olfactory acceptable amount of chirally enriched molecules of the general formula (I) prepared by the process as claimed in claim 1,
wherein the cosmetic composition is enriched with (2R, 4R) isomer of 2,4-disubstituted-tetrahydropyran-4-ol.

5. A fragrance composition containing chirally enriched molecules of the general formula (I) prepared by the process as claimed in claim 2 with at least one perfume and/or at least one cologne and/or at least one eau du toilette and/or at least one eau du parfum and/or at least one cosmetic and/or at least one personal care product and/or at least one cleansing product and/or at least one fabric softener and/or at least one air freshener,
wherein the fragrance composition is enriched with acylated (2R, 4R) isomer of 2,4-disubstituted-tetrahydropyran-4-ol.

6. A cosmetic composition containing an olfactory acceptable amount of chirally enriched molecules of the general formula (I) prepared by the process as claimed in claim 2,
wherein the fragrance composition is enriched with acylated (2R, 4R) isomer of 2,4-disubstituted-tetrahydropyran-4-ol.

* * * * *